United States Patent
Sturesson

(10) Patent No.: US 12,372,673 B2
(45) Date of Patent: Jul. 29, 2025

(54) X-RAY SENSING DETECTOR ASSEMBLY

(71) Applicant: RTI GROUP AB, Mölndal (SE)

(72) Inventor: Sören Sturesson, Lerum (SE)

(73) Assignee: RTI GROUP AB, Mölndal (SE)

( * ) Notice: Subject to any disclaimer, the term of this patent is extended or adjusted under 35 U.S.C. 154(b) by 215 days.

(21) Appl. No.: 17/917,162

(22) PCT Filed: May 18, 2021

(86) PCT No.: PCT/EP2021/063148
§ 371 (c)(1),
(2) Date: Oct. 5, 2022

(87) PCT Pub. No.: WO2021/239514
PCT Pub. Date: Dec. 2, 2021

(65) Prior Publication Data
US 2023/0161058 A1 May 25, 2023

(30) Foreign Application Priority Data

May 25, 2020 (SE) .................... 2050598-8

(51) Int. Cl.
*G01T 1/24* (2006.01)
*G01T 1/02* (2006.01)
(52) U.S. Cl.
CPC .............. *G01T 1/244* (2013.01); *G01T 1/026* (2013.01)
(58) Field of Classification Search
CPC ................................................... G01T 1/244
See application file for complete search history.

(56) References Cited

U.S. PATENT DOCUMENTS 3,535,520 A  10/1970 Higatsberger et al.
4,988,866 A   1/1991 Westerlund
(Continued)

FOREIGN PATENT DOCUMENTS

CN   110174692 A   8/2019
EP     2196825 A1  6/2010
(Continued)

OTHER PUBLICATIONS

International Search Report and Written Opinion for Application No. PCT/EP2021/063148, dated Aug. 26, 2021.
(Continued)

*Primary Examiner* — Carolyn Fin
(74) *Attorney, Agent, or Firm* — MARSHALL, GERSTEIN & BORUN LLP

(57) ABSTRACT

The invention concerns an X-ray sensing detector assembly, wherein the detector assembly comprises: at least one primary X-ray sensing member; and an X-ray blocking detector housing surrounding the at least one primary X-ray sensing member, wherein a first, upper side of the detector housing is provided with an X-ray window allowing passage of X-rays into the detector housing so as to allow X-rays directed towards the first, upper side of the detector housing to pass through the X-ray window and interact with the at least one primary X-ray sensing member. The detector assembly is provided with at least one secondary X-ray sensing member arranged outside of the detector housing, wherein an X-ray blocking element is arranged on an upper side of the secondary X-ray sensing member so as to prevent that the secondary X-ray sensing member is exposed to X-rays directed towards the first, upper side of the detector housing.

10 Claims, 1 Drawing Sheet

(56) References Cited

U.S. PATENT DOCUMENTS

| | | | |
|---|---|---|---|
| 9,535,165 | B2 | 1/2017 | Takatori |
| 11,052,266 | B2 * | 7/2021 | Roberts ................ G01T 1/2914 |
| 2009/0294678 | A1 | 12/2009 | Frank |
| 2019/0242834 | A1 | 8/2019 | Rothschild et al. |

FOREIGN PATENT DOCUMENTS

| | | |
|---|---|---|
| ES | 2453484 T3 | 4/2014 |
| JP | H08320527 A | 12/1996 |
| JP | 2013096759 A | 5/2013 |
| WO | WO-2012178042 A2 | 12/2012 |
| WO | WO-2014196914 A1 | 12/2014 |

OTHER PUBLICATIONS

Written Opinion of the International Preliminary Examining Authority for Application No. PCT/EP2021/063148, dated Jan. 4, 2022.
Office Action in corresponding Application No. SE 2050598-8, dated Feb. 5, 2021.
International Preliminary Report on Patentability for Application No. PCT/EP2021/063148, dated Aug. 29, 2022.

* cited by examiner

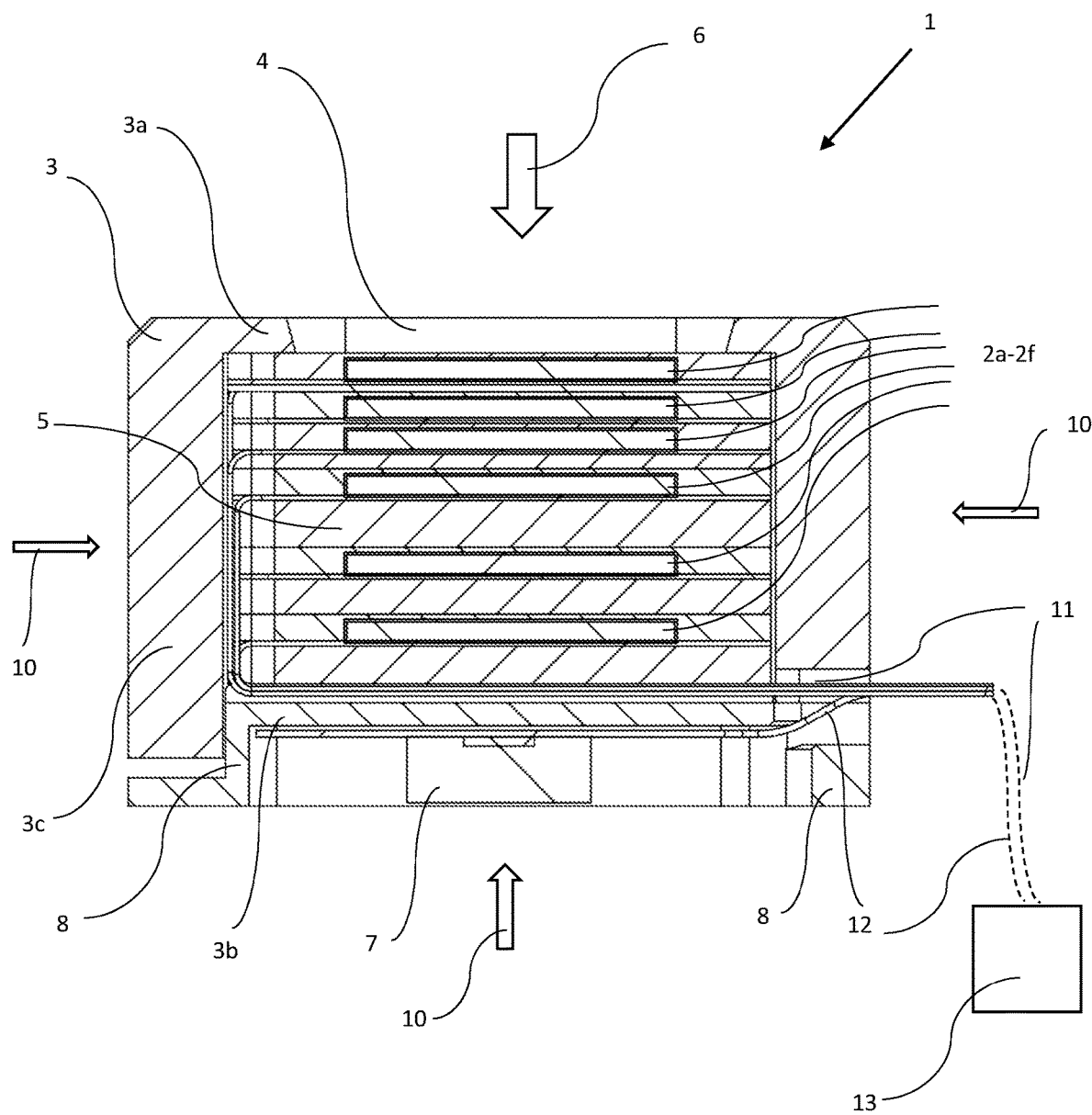

X-RAY SENSING DETECTOR ASSEMBLY

TECHNICAL FIELD

This invention relates to an X-ray sensing detector assembly according to the preamble of claim 1. In particular, the invention relates to an X-ray sensing detector assembly for use in quality assurance assessments of a medical X-ray equipment.

BACKGROUND OF THE INVENTION

Medical X-ray equipment are regularly subject to quality assurance assessments. Such assessments include determining radiation output (exposure or air karma), tube potential of the X-ray source, total filtration (attenuation) of the X-ray beam, and half-value layer of the X-ray beam at a position where a patient is located during operation of the equipment. These properties can then be used to validate the operation of the X-ray equipment.

An example of a suitable device for measuring and determining such properties is a stacked detector having a plurality of X-ray sensing diodes arranged in layers with various attenuating filters arranged between the diode layers, where the stacked diodes are arranged in an X-ray blocking housing provided with an opening (X-ray window) arranged above the layered diode structure. The opening is intended to be directed towards the X-ray source when the device is arranged in the beam so as to allow only primary radiation, i.e. radiation emitted directly from the X-ray source, to enter the housing and interact with the diode layers therein so as to generate electric signals in the diode layers corresponding to the primary radiation as a result of the interaction. The diodes are connected to electronic components allowing processing and evaluation of the signals emitted from the diodes and further allowing determination of the X-ray equipment properties of interest. Detectors of this type, i.e. stacked diode detectors arranged behind an opening/window in a radiation protection housing, have been in use for many years. An example of a detector of this type is disclosed in WO2014/196914.

Although detectors of the above type are suitable for determining the properties mentioned above, the directional dependence of these detectors (i.e. the dependence on in which direction the housing opening/window is facing) makes them less suitable for determining other properties relevant for medical X-ray equipment. This is exemplified in WO2014/196914 where several detectors are needed or one detector needs to be moved around between different positions of the X-ray equipment to measure and determine different aspects of the X-ray radiation.

There is thus a need for improvements in this field.

SUMMARY OF THE INVENTION

An object of this invention is to provide an X-ray sensing detector assembly for e.g. quality assurance of medical X-ray equipment that exhibit improved functionality compared to conventional detectors. This object is achieved by the detector assembly defined by the technical features contained in independent claim 1. The dependent claims contain advantageous embodiments, further developments and variants of the invention.

The invention concerns an X-ray sensing detector assembly, wherein the detector assembly comprises: at least one primary X-ray sensing member; and an X-ray blocking detector housing surrounding the at least one primary X-ray sensing member, wherein a first, upper side of the detector housing is provided with an X-ray window allowing passage of X-rays into the detector housing so as to allow X-rays directed towards the first, upper side of the detector housing to pass through the X-ray window and interact with the at least one primary X-ray sensing member.

Further, the detector assembly is provided with at least one secondary X-ray sensing member arranged outside of the detector housing, wherein an X-ray blocking element is arranged on an upper side of the secondary X-ray sensing member so as to prevent that the secondary X-ray sensing member is exposed to X-rays directed towards the first, upper side of the detector housing.

This means that when the detector assembly is placed in an X-ray beam with the X-ray window directed towards the X-ray source, typically when placed onto a phantom positioned where a patient is positioned in a medical X-ray equipment during normal operation of the equipment, the primary X-ray sensing member(s) arranged inside the detector housing can be used to, in line with conventional detectors, determine the above mentioned properties of the medical X-ray equipment and from these properties calculate various primary parameters. The secondary X-ray sensing member(s) provide(s) for the possibility to simultaneously measure and determine secondary dose parameters generated by secondary, scattered radiation, i.e. X-ray radiation that is not primary radiation directed from the X-ray source towards the detector housing X-ray window but instead is scattered radiation directed sideways and/or in an opposite direction (or in some angle there between) in relation to the direction of the primary radiation. A main part of the scattered secondary radiation is normally a result of backscattering from the patient or phantom located below the detector assembly and is thus directed towards an underside of the detector assembly in a direction more or less opposite to that of the primary radiation.

A detector assembly of the inventive type can thus be used to simultaneously measure and determine total dose parameters including both primary (incident) and secondary (scattered) radiation. Separate signals from the first and the second X-ray sensing members can be used to present a result of primary dose parameters and secondary dose parameters separately or as a sum.

Conventionally, the contribution of the secondary radiation to the total dose is estimated from standardized tables, which introduces uncertainties, or is determined from an additional measurement with another type of detector, which requires additional time and work. The inventive detector assembly thus provides a more accurate result and/or is more time and cost efficient.

The detector housing and the X-ray blocking element is preferably made of e.g. tin (Sn) or tungsten (W) or other material of high atomic number that efficiently attenuates (blocks) X-ray radiation. Upper, lower and wall segments of the detector housing, as well as the X-ray blocking element, may have a thickness of e.g. 1-3 mm. The underside of the secondary X-ray sensing member is preferably free from any X-ray blocking material. Also the sides of the secondary X-ray sensing member may be free from such material.

The secondary X-ray sensing member is preferably attached to the detector housing so as to form one integrated component, which simplifies handling.

The detector assembly preferably comprises a plastic housing surrounding the detector housing and the secondary X-ray sensing member. Such a plastic housing may also surround e.g. signal processing electronic components and electric connections for transferring signals from the sensing members to the electronic components.

In an embodiment the secondary X-ray sensing member is arranged on a second, lower side of the detector housing opposite to the first, upper side thereof. In such a case some part or parts of the detector housing can act as the X-ray blocking element. No separate X-ray blocking element is then required, which provides for making the detector assembly more compact (compared to if the secondary X-ray sensing member is arranged at a side of the housing). Typically, at least a bottom/lower segment of the detector housing will act as the X-ray blocking element. Also an upper segment of the detector housing may act as X-ray blocking element for the secondary X-ray sensing member depending on its position in relation to the X-ray window.

In an embodiment X-ray blocking material is arranged laterally around the secondary X-ray sensing member. This way the secondary X-ray sensing member is shielded from scattered radiation directed sideways towards the detector housing, which makes the secondary sensing member exposed mainly to backscattered radiation directed "upwards", within a solid angle, towards the underside of the detector housing. Such laterally arranged material also protects the secondary X-ray sensing member from impacts and may contribute to make the detector compact. If also sideways directed scattered radiation is to be measured, it is typically an advantage not to use such laterally arranged material. Alternatively, the laterally arranged blocking material may be provided with openings (X-ray windows) and/or the detector assembly may be provided with further secondary X-ray sensing members directed sideways (e.g. arranged onto sides of the detector housing or the laterally arranged X-ray blocking material).

In an embodiment the at least one primary X-ray sensing member is provided with a first electric connection for transferring of sensing member signals, wherein the secondary X-ray sensing member is provided with a second electric connection for transferring of sensing member signals, and wherein the first and second electric connections are separated from each other so as to allow separate processing of the signals from the primary and the secondary X-ray sensing members. This provides for separate connection of the first and second electric connections to a signal processing unit or similar, which in turn provides for determination of primary dose parameters and secondary dose parameters separate or as a sum. The electric connections may be arranged on flex/rigid boards that also may function as carriers for the X-ray sensing members.

In an embodiment the electric connections extend out from the detector housing. Thus, the detector housing is provided with at least one opening through which the electric connections extend. The electric connections can thereby be connected to signal processing electronic components arranged outside of detector housing.

In an embodiment the at least one primary X-ray sensing member has a flat shape with opposite main sides, wherein one of the main sides faces the X-ray window.

In an embodiment the detector assembly comprises a plurality of flat primary X-ray sensing members arranged in a layered structure. Preferably, attenuating elements are arranged between the layers of primary X-ray sensing members. Preferably, wherein each primary X-ray sensing member is provided with a corresponding electric connection for connection to signal processing electronic components. This provides for determination of the energy distribution of the photons in the X-radiation.

In an embodiment the at least one primary X-ray sensing member is a silicon diode. Preferably, also the secondary X-ray sensing unit is a silicon diode. Such diodes are suitable for a detector assembly to be used for analysing properties of medical X-ray equipment.

In an embodiment the detector housing has the general shape of a parallelepiped, such as a cube, a square cube or a rectangular cuboid, having an upper segment provided with the X-ray window, a lower segment, below which the secondary X-ray sensing member preferably is located, and four walls connecting the upper and lower segments.

BRIEF DESCRIPTION OF DRAWINGS

In the description of the invention given below reference is made to the following figure, in which:

FIG. 1 shows, in a sectional view, an example embodiment of an X-ray sensing detector assembly according to this disclosure.

DESCRIPTION OF EXAMPLE EMBODIMENTS OF THE INVENTION

FIG. 1 shows a sectional view of an example embodiment of an X-ray sensing detector assembly 1 according to this disclosure. The detector assembly 1 comprises in this example six primary X-ray sensing members 2a-2f and an X-ray blocking detector housing 3 surrounding the primary X-ray sensing members 2a-2f.

The detector housing 3 has the general shape of a rectangular cuboid having an upper side/segment 3a provided with an X-ray window 4, a lower side/segment 3b and four walls 3c connecting the upper and lower segments 3a, 3b. The segments and walls 3a-3c are in this example made of tin (Sn) and have a thickness of 1-3 mm. The segments and walls 3a-3c prevent X-radiation from entering the detector housing 3 (besides through the X-ray window 4, see below).

Each of the six primary X-ray sensing members 2a-2f has a flat shape with opposite main sides, wherein one of the main sides faces the X-ray window 4, i.e. upwards in FIG. 1. The detector assembly 1 thus comprises a plurality of flat primary X-ray sensing members 2a-2f arranged in a layered structure. The primary X-ray sensing member located closest to the X-ray window 4 is denoted 2a, the next one 2b, etc. Each of the primary X-ray sensing members 2a-2f is a silicon diode.

Attenuating elements 5 are arranged between the layers of primary X-ray sensing members 2a-2f. (Only one of the attenuating elements has been given a reference number in FIG. 1, but flat attenuating elements are in this example placed between all adjacent pairs of X-ray sensing members 2a-2f.) The attenuating elements may be made of different material and may have different thickness, as indicated in FIG. 1.

The detector assembly 1 is further provided with a (in this example one) secondary X-ray sensing member 7 arranged outside of the detector housing 3. An X-ray blocking element, in this example at least the lower segment 3b of the detector housing 3, is arranged on an upper side of the secondary X-ray sensing member 7 so as to prevent that the secondary X-ray sensing member 7 is exposed to X-rays directed towards the first, upper side 3a of the detector housing 3. As shown in FIG. 1, the secondary X-ray sensing member 7 is arranged on the second, lower side 3b of the detector housing 3 opposite to the first, upper side 3a thereof. X-ray blocking material 8 is also arranged laterally around the secondary X-ray sensing member 7 at the second, lower side 3b of the detector housing 3. Also the secondary X-ray sensing member 7 is in this example a silicon diode.

Each of the primary X-ray sensing members 2a-2f is provided with a corresponding electric connection 11 for transferring of sensing member signals. The reference number 11 thus refers to six separate electric connections. The secondary X-ray sensing member 7 is also provided with a separate electric connection 12 for transferring of sensing member signals. All electric connections are separated from each other so as to allow separate processing of the signals from the individual primary X-ray sensing members 2a-2f and from the secondary X-ray sensing member 7.

The electric connections 11, 12 extend out from the detector housing 3 and are connected to schematically indicated signal processing electronic components 13 arranged outside of detector housing 3. The electronic components 13 include e.g. amplifiers, A/D converters and other components well known in the art.

The detector assembly 1 further comprises a plastic housing (not shown) that surrounds the detector housing 3, the electric connections 11, 12 and the signal processing electronic components 13, so as to form one single unit that is easy to handle.

The X-ray window 4, which is provided on the upper side 3a of the detector housing 3, allows passage of X-rays into the detector housing 3. When in use, the detector assembly is typically arranged so that the X-ray window 4 is directed towards the X-ray source so that primary (incident) X-radiation 6 is directed more or less perpendicular towards the upper side 3a of the housing 3 and the X-ray window 4. Primary X-radiation 6 may thus pass through the X-ray window 4 and interact with the primary X-ray sensing members 2a-2f. Information on energy distribution of the primary X-radiation can be obtained from the layered arrangement of sensing members 2a-2f and attenuation members 5. Primary radiation 6 passing through also the last primary X-ray sensing member 2f is finally attenuated (to negligible levels) by the lower segment 3b of the detector housing 3.

Operation of the X-ray source generates also secondary, scattered radiation 10 that will be directed in various directions. As the detector housing 3 and the blocking material 8 shields the secondary X-ray sensing member 7 from radiation directed downwards and sideways towards the detector assembly 1 (with reference to FIG. 1), the secondary X-ray sensing member 7 will mainly be exposed to and measure scattered radiation 10 directed upwards (within some solid angle) towards the lower side 3b of the detector housing 3. That is, the secondary X-ray sensing member 7 will mainly be exposed to and measure backscatter from a phantom (or patient) located below the detector assembly 1.

The detector assembly 1 can thereby simultaneously measure both the properties of the primary X-radiation 6 as well the scattered radiation 10, in particular backscattering, and provide dose parameters for both primary and (back) scattered radiation, separately or as a sum.

The invention is not limited by the embodiments described above but can be modified in various ways within the scope of the claims. For instance, the detector housing 3 and the X-ray blocking element 3b and material 8 may be made of e.g. tungsten (W) or other material of high atomic number that efficiently attenuates X-ray radiation.

Moreover, the secondary X-ray sensing member 7 need not necessarily be located below the detector housing 3 but may be located at a side of the detector housing 3 below an X-ray blocking element so as to protect the secondary X-ray sensing member 7 from the primary radiation 6 during use of the detector assembly 1.

In order to measure also sideways directed scattered radiation, the detector assembly 1 may be designed without X-ray blocking material 8 that laterally surrounds the secondary X-ray sensing member 7. If such a lateral frame still is of interest, e.g. for protecting the secondary X-ray sensing member 7 from impacts, the frame may be made of e.g. a plastic material. However, in the example shown in FIG. 1 the "field-of-view" of the secondary X-ray sensing member 7, i.e. the solid angle within which the secondary X-ray sensing member 7 is capable of detecting more or less upwardly directed scattered radiation, is sufficient for most applications.

The invention claimed is:

1. An X-ray sensing detector assembly, wherein the detector assembly comprises:
   at least one primary X-ray sensing member; and
   an X-ray blocking detector housing surrounding the at least one primary X-ray sensing member,
   wherein a first, upper side of the detector housing is provided with an X-ray window allowing passage of X-rays into the detector housing so as to allow X-rays directed towards the first, upper side of the detector housing to pass through the X-ray window and interact with the at least one primary X-ray sensing member,
   characterized in
   that the detector assembly is provided with at least one secondary X-ray sensing member arranged outside of the detector housing,
   wherein an X-ray blocking element is arranged on an upper side of the secondary X-ray sensing member so as to prevent that the secondary X-ray sensing member is exposed to X-rays directed towards the first, upper side of the detector housing,
   wherein the at least one primary X-ray sensing member has a flat shape with opposite main sides, wherein one of the main sides faces the X-ray window,
   wherein the detector assembly comprises a plurality of flat primary X-ray sensing members arranged in a layered structure, and
   wherein attenuating elements are arranged between the layers of primary X-ray sensing members.

2. The X-ray sensing detector assembly according to claim 1, wherein the secondary X-ray sensing member is arranged on a second, lower side of the detector housing opposite to the first, upper side thereof.

3. The X-ray sensing detector assembly according to claim 1, wherein X-ray blocking material is arranged laterally around the secondary X-ray sensing member.

4. The X-ray sensing detector assembly according to claim 1, wherein the at least one primary X-ray sensing member is provided with a first electric connection for transferring of sensing member signals, wherein the secondary X-ray sensing member is provided with a second electric connection for transferring of sensing member signals, and wherein the first and second electric connections are separated from each other so as to allow separate processing of the signals from the primary and the secondary X-ray sensing members.

5. The X-ray sensing detector assembly according to claim 4, wherein the electric connections extend out from the detector housing.

6. The X-ray sensing detector assembly according to claim 4, wherein the electric connections are connected to signal processing electronic components arranged outside of detector housing.

7. The X-ray sensing detector assembly according to claim 1, wherein each primary X-ray sensing member is provided with a corresponding electric connection for connection to signal processing electronic components.

8. The X-ray sensing detector assembly according to claim 1, wherein the at least one primary X-ray sensing member is a silicon diode.

9. The X-ray sensing detector assembly according to claim 1, wherein the secondary X-ray sensing unit is a silicon diode.

10. The X-ray sensing detector assembly according to claim 1, wherein the detector housing has the general shape of a parallelepiped, such as a cube, a square cube or a rectangular cuboid, having an upper segment provided with the X-ray window, a lower segment, below which the secondary X-ray sensing member preferably is located, and four walls connecting the upper and lower segments.

* * * * *